(12) United States Patent
Derose et al.

(10) Patent No.: US 7,982,092 B2
(45) Date of Patent: *Jul. 19, 2011

(54) CHIMERIC GENE COMPRISING INTRON FROM HISTONE H3.3 GENE

(75) Inventors: Richard Derose, Lyons (FR); Nicole Chaubet, legal reprsentative, Strasbourg (FR); Claude Gigot, Strasbourg (FR)

(73) Assignee: Bayer Cropscience SA, Lyons (FR)

( * ) Notice: Subject to any disclaimer, the term of this patent is extended or adjusted under 35 U.S.C. 154(b) by 668 days.

This patent is subject to a terminal disclaimer.

(21) Appl. No.: 11/797,078

(22) Filed: Apr. 30, 2007

(65) Prior Publication Data

US 2009/0328247 A1 Dec. 31, 2009

Related U.S. Application Data

(60) Division of application No. 10/023,839, filed on Dec. 21, 2001, now abandoned, which is a continuation of application No. 09/000,062, filed as application No. PCT/FR96/01109 on Jul. 17, 1996, now Pat. No. 6,338,961.

(30) Foreign Application Priority Data

Jul. 19, 1995 (FR) .................................... 95 08980

(51) Int. Cl.
*C12N 15/82* (2006.01)
*A01H 5/00* (2006.01)
*C07H 21/00* (2006.01)

(52) U.S. Cl. ....... 800/278; 800/295; 800/298; 536/24.1; 536/23.1

(58) Field of Classification Search ......................... None
See application file for complete search history.

(56) References Cited

U.S. PATENT DOCUMENTS

| | | | |
|---|---|---|---|
| 4,535,060 A | 8/1985 | Comai | |
| 4,971,908 A | 11/1990 | Kishore et al. | |
| 5,491,288 A | 2/1996 | Chaubet et al. | |
| 5,510,471 A | 4/1996 | Lebrun et al. | |
| 5,635,618 A | 6/1997 | Capellades et al. | |
| 6,338,961 B1 * | 1/2002 | DeRose et al. ............. | 435/320.1 |

FOREIGN PATENT DOCUMENTS

| | | |
|---|---|---|
| EP | 0 507 698 | 10/1992 |
| EP | 0 508 909 | 10/1992 |
| EP | 0 652 286 | 5/1995 |
| WO | WO 95/06128 | 3/1995 |

OTHER PUBLICATIONS

Kanazin et al. Organization of the histone H3 genes in soybean, barley and wheat. (1996) MGG; vol. 250; pp. 137-147.*
Chaubet et al., "Gene Encoding a Histone H3.3-like Variant in Arabidopsis Contain Intervening Sequences" Journal of Molecular Biology, 1992, vol. 225, pp. 569-574, Academic Press Limited, USA.
Choi et al., "A Generic Intron Increases Gene Expression in Transgenic Mice" Molecular and Cellular Biology, 1991, vol. 11, No. 6, pp. 3070-3074, American Society for Microbiology USA.
Cornejo et al., "Activity of a Maize Ubiquitin Promoter in Transgenic Rice" Plant Molecular Biology, 1993, vol. 23, pp. 567-581, Kluwer Academic Publishers, Belgium.
Jayawardene et al., "Molecular Cloning, Sequence Analysis and Differential Expression of an Intron-containing Gene Encoding Tomato Histone H1" Eur. J. Bioch., 1994, vol. 223, pp. 693-699, FEBS, Canada.
Seiler-Tuyns et al., "A chimeric mouse histone H4 gene containing either an intron or poly(A) addition signal behaves like a basal histone" Nucleic Acids Research, 1986, vol. 14, No. 22, pp. 8845-8862, Oxford University Press, United Kingdom.
Sinibaldi et al., "Intron splicing and intron-mediated enhanced expression in monocots" Progress in Nucleic Acid Research and Molecular Biology, 1992, vol. 42, pp. 229-257, Academic Press, USA.
Sundas et al., "cDNA sequence and expression of an intron-containing histone H2A gene from Norway spruce, *Picea abies*" Plant Molecular Biology, 1993, vol. 21, No. 4, pp. 595-605, Kluwer Academic Publishers, The Netherlands.

* cited by examiner

*Primary Examiner* — Cathy Kingdon Worley
(74) *Attorney, Agent, or Firm* — Buchanan Ingersoll & Rooney PC

(57) ABSTRACT

An isolated DNA sequence capable of serving as regulatory element in a chimeric gene which can be used for the transformation of plants is disclosed. A chimeric gene containing the DNA sequence as a regulatory element for the transformation of plants is also disclosed. The gene comprises at least, in the direction of transcription, a promoter sequence, a transgene and a regulatory element, characterized in that the regulatory element comprises an intron from the noncoding 5' region of a plant histone gene, allowing the expression of the protein in the zones undergoing rapid growth. The production of transgenic plants is also disclosed.

12 Claims, No Drawings

SEQUENCE LISTING

<160> NUMBER OF SEQ ID NOS: 22

<210> SEQ ID NO 1
<211> LENGTH: 1713
<212> TYPE: DNA
<213> ORGANISM: Zea mays

<400> SEQUENCE: 1

```
aatcaatttc acacaggaaa cagctatgac catgattacg aattcgggcc cgggcgcgtg      60
atccggcggc ggcagcggcg gcggcggtgc aggcgggtgc cgaggagatc gtgctgcagc     120
ccatcaagga gatctggggc agcgtcaagc tgccggggtc caagtcgctt ccaaccgga      180
tcctcctact cgccgccctg tccgagggga acagtggt tgataacctg ctgaacagtg       240
aggatgtcca ctacatgctc ggggccttga ggactcttgg tctctctgtc gaagcggaca     300
aaggtcccaa aagagctgta cttgttggct ctggtgaaaa gttcccagtt gaggatgcta     360
agaggaagt gcagctcttc ttggggaatg ctggaactgc aatgcggcca ttgacagcag     420
ctgttactgc tgctggtgga aatgcaactt acgtgcttga tggagtacca agaatgaggg     480
agagacccat tggcgacttg gttgtcggat tgaagcagct tggtgcagat gttgattgtt     540
tccttggcac tgactgccca cgtgttcgtg tcaatggaat cggagggcta cctggtggca     600
aggtcaagct gtctggctcc atcagcagtc agtacttgag tgccttgctg atggctgctc     660
ctttggctct tggggatgtg gagattgaaa tcattgataa attaatctcc attccgtacg     720
tcgaaatgac attgagattg atggaccgtt ttggtgtgaa agcagagcat tctgatagct     780
gggacagatt ctacattaag ggaggtcaaa aatacaagtc ccctaaaaat gcctatgttg     840
aaggtgatgc ctcaagcgca agctatttct tggctggtgc tgcaattact ggagggactg     900
tgactgtgga aggttgtggc accaccagtt gcagggtga tgtgaagttt gctgaggtac     960
tggagatgat gggagcgaag gttacatgga ccgagactag cgtaactgtt actccccac     1020
cgcgggagcc atttgggagg aaacaccctca aggcgattga tgtcaacatc aacaagatgc    1080
ctgatgtcgc catgactctt gctgtggttg ccctcttttgc cgatggcccg acagccatca    1140
gagacgtggc ttcctggaga gtaaaggaga ccgagaggat ggttgcgatc cggacggagc    1200
taaccaagct gggagcatct gttgaggaag ggccggacta ctgcatcatc acgccgccgg    1260
agaagctgaa cgtgacggcg atcgacacgt acgacgacca caggatggcc atggccttct    1320
cccttgccgc ctgtgccgag gtccccgtca ccatccggga cctgggtgc acccggaaga    1380
ccttccccga ctacttcgat gtgctgagca ctttcgtcaa gaattaataa agcgtgcgat    1440
actaccacgc agcttgattg aagtgatagg cttgtgctga ggaaatacat ttctttttgt   1500
ctgttttct ctttcacggg attaagtttt gagtctgtaa cgttagttgt ttgtagcaag    1560
tttctatttc ggatcttaag tttgtgcact gtaagccaaa tttcatttca agagtggttc    1620
gttggaataa taagaataat aaattacgtt tcagtgaaaa aaaaaaaaaa aaaaaaaaaa    1680
aaaaaaaaa aaaaaaaaaa aacccgggaa ttc                                  1713
```

<210> SEQ ID NO 2
<211> LENGTH: 1340
<212> TYPE: DNA
<213> ORGANISM: Zea mays
<220> FEATURE:
<221> NAME/KEY: CDS
<222> LOCATION: (6)..(1337)

<400> SEQUENCE: 2

```
ccatg gcc ggc gcc gag gag atc gtg ctg cag ccc atc aag gag atc tcc        50
      Ala Gly Ala Glu Glu Ile Val Leu Gln Pro Ile Lys Glu Ile Ser
      1               5                  10                  15 ggc acc gtc aag ctg ccg ggg tcc aag tcg ctt tcc aac cgg atc ctc          98
Gly Thr Val Lys Leu Pro Gly Ser Lys Ser Leu Ser Asn Arg Ile Leu
                 20                  25                  30 cta ctc gcc gcc ctg tcc gag ggg aca aca gtg gtt gat aac ctg ctg        146
Leu Leu Ala Ala Leu Ser Glu Gly Thr Thr Val Val Asp Asn Leu Leu
         35                  40                  45 aac agt gag gat gtc cac tac atg ctc ggg gcc ttg agg act ctt ggt        194
Asn Ser Glu Asp Val His Tyr Met Leu Gly Ala Leu Arg Thr Leu Gly
 50                  55                  60 ctc tct gtc gaa gcg gac aaa gct gcc aaa aga gct gta gtt gtt ggc        242
Leu Ser Val Glu Ala Asp Lys Ala Ala Lys Arg Ala Val Val Val Gly
 65                  70                  75 tgt ggt gga aag ttc cca gtt gag gat gct aaa gag gaa gtg cag ctc        290
Cys Gly Gly Lys Phe Pro Val Glu Asp Ala Lys Glu Glu Val Gln Leu
 80                  85                  90                  95 ttc ttg ggg aat gct gga act gca atg cgg cca ttg aca gca gct gtt        338
Phe Leu Gly Asn Ala Gly Thr Ala Met Arg Pro Leu Thr Ala Ala Val
             100                 105                 110 act gct gct ggt gga aat gca act tac gtg ctt gat gga gta cca aga        386
Thr Ala Ala Gly Gly Asn Ala Thr Tyr Val Leu Asp Gly Val Pro Arg
         115                 120                 125 atg agg gag aga ccc att ggc gac ttg gtt gtc gga ttg aag cag ctt        434
Met Arg Glu Arg Pro Ile Gly Asp Leu Val Val Gly Leu Lys Gln Leu
         130                 135                 140 ggt gca gat gtt gat tgt ttc ctt ggc act gac tgc cca cct gtt cgt        482
Gly Ala Asp Val Asp Cys Phe Leu Gly Thr Asp Cys Pro Pro Val Arg
145                 150                 155 gtc aat gga atc gga ggg cta cct ggt ggc aag gtc aag ctg tct ggc        530
Val Asn Gly Ile Gly Gly Leu Pro Gly Gly Lys Val Lys Leu Ser Gly
160                 165                 170                 175 tcc atc agc agt cag tac ttg agt gcc ttg ctg atg gct gct cct ttg        578
Ser Ile Ser Ser Gln Tyr Leu Ser Ala Leu Leu Met Ala Ala Pro Leu
                 180                 185                 190 gct ctt ggg gat gtg gag att gaa atc att gat aaa tta atc tcc att        626
Ala Leu Gly Asp Val Glu Ile Glu Ile Ile Asp Lys Leu Ile Ser Ile
         195                 200                 205 ccg tac gtc gaa atg aca ttg aga ttg atg gag cgt ttt ggt gtg aaa        674
Pro Tyr Val Glu Met Thr Leu Arg Leu Met Glu Arg Phe Gly Val Lys
         210                 215                 220 gca gag cat tct gat agc tgg gac aga ttc tac att aag gga ggt caa        722
Ala Glu His Ser Asp Ser Trp Asp Arg Phe Tyr Ile Lys Gly Gly Gln
225                 230                 235 aaa tac aag tcc cct aaa aat gcc tat gtt gaa ggt gat gcc tca agc        770
Lys Tyr Lys Ser Pro Lys Asn Ala Tyr Val Glu Gly Asp Ala Ser Ser
240                 245                 250                 255 gca agc tat ttc ttg gct ggt gct gca att act gga ggg act gtg act        818
Ala Ser Tyr Phe Leu Ala Gly Ala Ala Ile Thr Gly Gly Thr Val Thr
                 260                 265                 270 gtg gaa ggt tgt ggc acc acc agt ttg cag ggt gat gtg aag ttt gct        866
Val Glu Gly Cys Gly Thr Thr Ser Leu Gln Gly Asp Val Lys Phe Ala
         275                 280                 285 gag gta ctg gag atg atg gga gcg aag gtt aca tgg acc gag act agc        914
Glu Val Leu Glu Met Met Gly Ala Lys Val Thr Trp Thr Glu Thr Ser
         290                 295                 300
```

```
gta act gtt act ggc cca ccg cgg gag cca ttt ggg agg aaa cac ctc      962
Val Thr Val Thr Gly Pro Pro Arg Glu Pro Phe Gly Arg Lys His Leu
305                 310                 315 aag gcg att gat gtc aac atg aac aag atg cct gat gtc gcc atg act     1010
Lys Ala Ile Asp Val Asn Met Asn Lys Met Pro Asp Val Ala Met Thr
320                 325                 330                 335 ctt gct gtg gtt gcc ctc ttt gcc gat ggc ccg aca gcc atc aga gac     1058
Leu Ala Val Val Ala Leu Phe Ala Asp Gly Pro Thr Ala Ile Arg Asp
                340                 345                 350 gtg gct tcc tgg aga gta aag gag acc gag agg atg gtt gcg atc cgg     1106
Val Ala Ser Trp Arg Val Lys Glu Thr Glu Arg Met Val Ala Ile Arg
            355                 360                 365 acg gag cta acc aag ctg gga gca tct gtt gag gaa ggg ccg gac tac     1154
Thr Glu Leu Thr Lys Leu Gly Ala Ser Val Glu Glu Gly Pro Asp Tyr
        370                 375                 380 tgc atc atc acg ccg ccg gag aag ctg aac gtg acg gcg atc gac acg     1202
Cys Ile Ile Thr Pro Pro Glu Lys Leu Asn Val Thr Ala Ile Asp Thr
385                 390                 395 tac gac gac cac agg atg gcc atg gcc ttc tcc ctt gcc gcc tgt gcc     1250
Tyr Asp Asp His Arg Met Ala Met Ala Phe Ser Leu Ala Ala Cys Ala
400                 405                 410                 415 gag gtc ccc gtc acc atc cgg gac cct ggg tgc acc cgg aag acc ttc     1298
Glu Val Pro Val Thr Ile Arg Asp Pro Gly Cys Thr Arg Lys Thr Phe
                420                 425                 430 ccc gac tac ttc gat gtg ctg agc act ttc gtc aag aat taa             1340
Pro Asp Tyr Phe Asp Val Leu Ser Thr Phe Val Lys Asn
                435                 440

<210> SEQ ID NO 3
<211> LENGTH: 444
<212> TYPE: PRT
<213> ORGANISM: Zea mays

<400> SEQUENCE: 3

Ala Gly Ala Glu Glu Ile Val Leu Gln Pro Ile Lys Glu Ile Ser Gly
 1               5                  10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Thr Ala Met Arg Pro Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190
```

```
Leu Gly Asp Val Glu Ile Glu Ile Asp Lys Leu Ile Ser Ile Pro
    195                 200                 205

Tyr Val Glu Met Thr Leu Arg Leu Met Glu Arg Phe Gly Val Lys Ala
    210                 215                 220

Glu His Ser Asp Ser Trp Asp Arg Phe Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

Ala Ile Asp Val Asn Met Asn Lys Met Pro Asp Val Ala Met Thr Leu
                325                 330                 335

Ala Val Val Ala Leu Phe Ala Asp Gly Pro Thr Ala Ile Arg Asp Val
            340                 345                 350

Ala Ser Trp Arg Val Lys Glu Thr Glu Arg Met Val Ala Ile Arg Thr
        355                 360                 365

Glu Leu Thr Lys Leu Gly Ala Ser Val Glu Glu Gly Pro Asp Tyr Cys
    370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440

<210> SEQ ID NO 4
<211> LENGTH: 1340
<212> TYPE: DNA
<213> ORGANISM: Zea mays
<220> FEATURE:
<221> NAME/KEY: CDS
<222> LOCATION: (6)..(1337)

<400> SEQUENCE: 4 ccatg gcc ggc gcc gag gag atc gtg ctg cag ccc atc aag gag atc tcc      50
      Ala Gly Ala Glu Glu Ile Val Leu Gln Pro Ile Lys Glu Ile Ser
      1               5                   10                  15 ggc acc gtc aag ctg ccg ggg tcc aag tcg ctt tcc aac cgg atc ctc        98
Gly Thr Val Lys Leu Pro Gly Ser Lys Ser Leu Ser Asn Arg Ile Leu
            20                  25                  30 cta ctc gcc gcc ctg tcc gag ggg aca aca gtg gtt gat aac ctg ctg       146
Leu Leu Ala Ala Leu Ser Glu Gly Thr Thr Val Val Asp Asn Leu Leu
        35                  40                  45 aac agt gag gat gtc cac tac atg ctc ggg gcc ttg agg act ctt ggt       194
Asn Ser Glu Asp Val His Tyr Met Leu Gly Ala Leu Arg Thr Leu Gly
    50                  55                  60 ctc tct gtc gaa gcg gac aaa gct gcc aaa aga gct gta gtt gtt ggc       242
Leu Ser Val Glu Ala Asp Lys Ala Ala Lys Arg Ala Val Val Val Gly
65                  70                  75
```

-continued

| | | |
|---|---|---|
| tgt ggt gga aag ttc cca gtt gag gat gct aaa gag gaa gtg cag ctc<br>Cys Gly Gly Lys Phe Pro Val Glu Asp Ala Lys Glu Glu Val Gln Leu<br>80                       85                         90                       95 | 290 |
| ttc ttg ggg aat gct gga atc gca atg cgg tcc ttg aca gca gct gtt<br>Phe Leu Gly Asn Ala Gly Ile Ala Met Arg Ser Leu Thr Ala Ala Val<br>                    100                        105                      110 | 338 |
| act gct gct ggt gga aat gca act tac gtg ctt gat gga gta cca aga<br>Thr Ala Ala Gly Gly Asn Ala Thr Tyr Val Leu Asp Gly Val Pro Arg<br>          115                       120                       125 | 386 |
| atg agg gag aga ccc att ggc gac ttg gtt gtc gga ttg aag cag ctt<br>Met Arg Glu Arg Pro Ile Gly Asp Leu Val Val Gly Leu Lys Gln Leu<br>     130                       135                       140 | 434 |
| ggt gca gat gtt gat tgt ttc ctt ggc act gac tgc cca cct gtt cgt<br>Gly Ala Asp Val Asp Cys Phe Leu Gly Thr Asp Cys Pro Pro Val Arg<br>145                       150                       155 | 482 |
| gtc aat gga atc gga ggg cta cct ggt ggc aag gtc aag ctg tct ggc<br>Val Asn Gly Ile Gly Gly Leu Pro Gly Gly Lys Val Lys Leu Ser Gly<br>160                       165                      170                 175 | 530 |
| tcc atc agc agt cag tac ttg agt gcc ttg ctg atg gct gct cct ttg<br>Ser Ile Ser Ser Gln Tyr Leu Ser Ala Leu Leu Met Ala Ala Pro Leu<br>                    180                       185                      190 | 578 |
| gct ctt ggg gat gtg gag att gaa atc att gat aaa tta atc tcc att<br>Ala Leu Gly Asp Val Glu Ile Glu Ile Ile Asp Lys Leu Ile Ser Ile<br>          195                       200                       205 | 626 |
| ccg tac gtc gaa atg aca ttg aga ttg atg gag cgt ttt ggt gtg aaa<br>Pro Tyr Val Glu Met Thr Leu Arg Leu Met Glu Arg Phe Gly Val Lys<br>     210                       215                       220 | 674 |
| gca gag cat tct gat agc tgg gac aga ttc tac att aag gga ggt caa<br>Ala Glu His Ser Asp Ser Trp Asp Arg Phe Tyr Ile Lys Gly Gly Gln<br>225                       230                       235 | 722 |
| aaa tac aag tcc cct aaa aat gcc tat gtt gaa ggt gat gcc tca agc<br>Lys Tyr Lys Ser Pro Lys Asn Ala Tyr Val Glu Gly Asp Ala Ser Ser<br>240                       245                       250                 255 | 770 |
| gca agc tat ttc ttg gct ggt gct gca att act gga ggg act gtg act<br>Ala Ser Tyr Phe Leu Ala Gly Ala Ala Ile Thr Gly Gly Thr Val Thr<br>                    260                       265                      270 | 818 |
| gtg gaa ggt tgt ggc acc acc agt ttg cag ggt gat gtg aag ttt gct<br>Val Glu Gly Cys Gly Thr Thr Ser Leu Gln Gly Asp Val Lys Phe Ala<br>          275                       280                       285 | 866 |
| gag gta ctg gag atg atg gga gcg aag gtt aca tgg acc gag act agc<br>Glu Val Leu Glu Met Met Gly Ala Lys Val Thr Trp Thr Glu Thr Ser<br>              290                       295                       300 | 914 |
| gta act gtt act ggc cca ccg cgg gag cca ttt ggg agg aaa cac ctc<br>Val Thr Val Thr Gly Pro Pro Arg Glu Pro Phe Gly Arg Lys His Leu<br>305                       310                       315 | 962 |
| aag gcg att gat gtc aac atg aac aag atg cct gat gtc gcc atg act<br>Lys Ala Ile Asp Val Asn Met Asn Lys Met Pro Asp Val Ala Met Thr<br>320                       325                       330                 335 | 1010 |
| ctt gct gtg gtt gcc ctc ttt gcc gat ggc ccg aca gcc atc aga gac<br>Leu Ala Val Val Ala Leu Phe Ala Asp Gly Pro Thr Ala Ile Arg Asp<br>                    340                       345                      350 | 1058 |
| gtg gct tcc tgg aga gta aag gag acc gag agg atg gtt gcg atc cgg<br>Val Ala Ser Trp Arg Val Lys Glu Thr Glu Arg Met Val Ala Ile Arg<br>          355                       360                       365 | 1106 |
| acg gag cta acc aag ctg gga gca tct gtt gag gaa ggg ccg gac tac<br>Thr Glu Leu Thr Lys Leu Gly Ala Ser Val Glu Glu Gly Pro Asp Tyr<br>              370                       375                      380 | 1154 |
| tgc atc atc acg ccg ccg gag aag ctg aac gtg acg gcg atc gac acg<br>Cys Ile Ile Thr Pro Pro Glu Lys Leu Asn Val Thr Ala Ile Asp Thr<br>385                       390                       395 | 1202 |

```
tac gac gac cac agg atg gcg atg gcc ttc tcc ctt gcc gcc tgt gcc    1250
Tyr Asp Asp His Arg Met Ala Met Ala Phe Ser Leu Ala Ala Cys Ala
400                 405                 410                 415 gag gtc ccc gtc acc atc cgg gac cct ggg tgc acc cgg aag acc ttc    1298
Glu Val Pro Val Thr Ile Arg Asp Pro Gly Cys Thr Arg Lys Thr Phe
            420                 425                 430 ccc gac tac ttc gat gtg ctg agc act ttc gtc aag aat taa            1340
Pro Asp Tyr Phe Asp Val Leu Ser Thr Phe Val Lys Asn
            435                 440

<210> SEQ ID NO 5
<211> LENGTH: 444
<212> TYPE: PRT
<213> ORGANISM: Zea mays

<400> SEQUENCE: 5
```

Ala Gly Ala Glu Glu Ile Val Leu Gln Pro Ile Lys Glu Ile Ser Gly
 1               5                  10                  15

Thr Val Lys Leu Pro Gly Ser Lys Ser Leu Ser Asn Arg Ile Leu Leu
            20                  25                  30

Leu Ala Ala Leu Ser Glu Gly Thr Thr Val Val Asp Asn Leu Leu Asn
        35                  40                  45

Ser Glu Asp Val His Tyr Met Leu Gly Ala Leu Arg Thr Leu Gly Leu
    50                  55                  60

Ser Val Glu Ala Asp Lys Ala Ala Lys Arg Ala Val Val Val Gly Cys
65                  70                  75                  80

Gly Gly Lys Phe Pro Val Glu Asp Ala Lys Glu Glu Val Gln Leu Phe
                85                  90                  95

Leu Gly Asn Ala Gly Ile Ala Met Arg Ser Leu Thr Ala Ala Val Thr
            100                 105                 110

Ala Ala Gly Gly Asn Ala Thr Tyr Val Leu Asp Gly Val Pro Arg Met
        115                 120                 125

Arg Glu Arg Pro Ile Gly Asp Leu Val Val Gly Leu Lys Gln Leu Gly
    130                 135                 140

Ala Asp Val Asp Cys Phe Leu Gly Thr Asp Cys Pro Pro Val Arg Val
145                 150                 155                 160

Asn Gly Ile Gly Gly Leu Pro Gly Gly Lys Val Lys Leu Ser Gly Ser
                165                 170                 175

Ile Ser Ser Gln Tyr Leu Ser Ala Leu Leu Met Ala Ala Pro Leu Ala
            180                 185                 190

Leu Gly Asp Val Glu Ile Glu Ile Ile Asp Lys Leu Ile Ser Ile Pro
        195                 200                 205

Tyr Val Glu Met Thr Leu Arg Leu Met Glu Arg Phe Gly Val Lys Ala
    210                 215                 220

Glu His Ser Asp Ser Trp Asp Arg Phe Tyr Ile Lys Gly Gly Gln Lys
225                 230                 235                 240

Tyr Lys Ser Pro Lys Asn Ala Tyr Val Glu Gly Asp Ala Ser Ser Ala
                245                 250                 255

Ser Tyr Phe Leu Ala Gly Ala Ala Ile Thr Gly Gly Thr Val Thr Val
            260                 265                 270

Glu Gly Cys Gly Thr Thr Ser Leu Gln Gly Asp Val Lys Phe Ala Glu
        275                 280                 285

Val Leu Glu Met Met Gly Ala Lys Val Thr Trp Thr Glu Thr Ser Val
    290                 295                 300

Thr Val Thr Gly Pro Pro Arg Glu Pro Phe Gly Arg Lys His Leu Lys
305                 310                 315                 320

```
Ala Ile Asp Val Asn Met Asn Lys Met Pro Asp Val Ala Met Thr Leu
            325                 330                 335

Ala Val Val Ala Leu Phe Ala Asp Gly Pro Thr Ala Ile Arg Asp Val
        340                 345                 350

Ala Ser Trp Arg Val Lys Glu Thr Glu Arg Met Val Ala Ile Arg Thr
    355                 360                 365

Glu Leu Thr Lys Leu Gly Ala Ser Val Glu Glu Gly Pro Asp Tyr Cys
370                 375                 380

Ile Ile Thr Pro Pro Glu Lys Leu Asn Val Thr Ala Ile Asp Thr Tyr
385                 390                 395                 400

Asp Asp His Arg Met Ala Met Ala Phe Ser Leu Ala Ala Cys Ala Glu
                405                 410                 415

Val Pro Val Thr Ile Arg Asp Pro Gly Cys Thr Arg Lys Thr Phe Pro
            420                 425                 430

Asp Tyr Phe Asp Val Leu Ser Thr Phe Val Lys Asn
        435                 440
```

```
<210> SEQ ID NO 6
<211> LENGTH: 418
<212> TYPE: DNA
<213> ORGANISM: Zea mays

<400> SEQUENCE: 6
tgaggtacga ttcttcgatc tctctttgatt ttcctggaaa tatttttttcg gtgatcgtga    60 aactactgga atcgctcgat aggtggtacg aaattaggcg agattagttt ctattcttgg   120
ccattatctt gtttcttcgc cgaatgatct tccgtataaa gattttaggt tagagatgaa   180
tcgtatagct agatttcatc accagatagt ttctttgtct agaatctctg aaattctcga   240 tagtttttcac atgtgtaaat agattgttct tattcggcga ttgttgatta gggttttgat   300
tttcttgatt atgcgattgc aattagggat tttctttggt tttgtgttga tcttacgata   360
cattcctgca attgaatacg tatggatcta aatcttgtta atttgttgaa cagatccc     418

<210> SEQ ID NO 7
<211> LENGTH: 494
<212> TYPE: DNA
<213> ORGANISM: Zea mays

<400> SEQUENCE: 7
ctcaggcgaa gaacaggtat gatttgtttg taattagatc aggggtttag gtctttccat    60 tacttttttaa tgtttttttct gttactgtct ccgcgatctg attttacgac aatagagttt   120
cgggttttgt cccattccag tttgaaaata acgtccgtc ttttaagttt gctggatcga   180
taaacctgtg aagattgagt ctagtcgatt tattggatga tccattcttc atcgtttttt   240
tcttgcttcg aagttctgta taaccagatt tgtctgtgtg cgattgtcat tacctagccg   300
tgtatcgaga actagggttt tcgagtcaat tttgccccctt ttggttatat ctggttcgat   360
aacgattcat ctggattagg gttttaagtg gtgacgttta gtattccaat ttcttcaaaa   420
tttagttatg gataatgaaa atcccgaatt gactgttcaa tttcttgtta aatgcgcaga   480
tcccgggatc tgcg                                                       494

<210> SEQ ID NO 8
<211> LENGTH: 20
<212> TYPE: DNA
<213> ORGANISM: Zea mays
```

```
<400> SEQUENCE: 8
gctctgctca tgtctgctcc                                              20

<210> SEQ ID NO 9
<211> LENGTH: 20
<212> TYPE: DNA
<213> ORGANISM: Zea mays

<400> SEQUENCE: 9
gcccgccctt gacaaagaaa                                              20

<210> SEQ ID NO 10
<211> LENGTH: 10
<212> TYPE: DNA
<213> ORGANISM: Zea mays

<400> SEQUENCE: 10
aattcccggg                                                         10

<210> SEQ ID NO 11
<211> LENGTH: 38
<212> TYPE: DNA
<213> ORGANISM: Zea mays

<400> SEQUENCE: 11
aattaagctc tagagtcgac ctgcaggcat gcaagctt                          38

<210> SEQ ID NO 12
<211> LENGTH: 41
<212> TYPE: DNA
<213> ORGANISM: Zea mays

<400> SEQUENCE: 12
gagccgagct ccatggccgg cgccgaggag atcgtgctgc a                      41

<210> SEQ ID NO 13
<211> LENGTH: 37
<212> TYPE: DNA
<213> ORGANISM: Zea mays

<400> SEQUENCE: 13
gcacgatctc ctcggcgccg gccatggagc tcggctc                           37

<210> SEQ ID NO 14
<211> LENGTH: 25
<212> TYPE: DNA
<213> ORGANISM: Zea mays

<400> SEQUENCE: 14
ccacaggatg gcgatggcct tctcc                                        25

<210> SEQ ID NO 15
<211> LENGTH: 33
<212> TYPE: DNA
<213> ORGANISM: Zea mays

<400> SEQUENCE: 15
gaatgctgga atcgcaatgc ggccattgac agc                               33

<210> SEQ ID NO 16
<211> LENGTH: 33
<212> TYPE: DNA
<213> ORGANISM: Zea mays
```

-continued

```
<400> SEQUENCE: 16
gaatgctgga actgcaatgc ggtccttgac agc                              33

<210> SEQ ID NO 17
<211> LENGTH: 34
<212> TYPE: DNA
<213> ORGANISM: Zea mays

<400> SEQUENCE: 17
cttggggaat gctgccatcg caatgcggcc attg                             34

<210> SEQ ID NO 18
<211> LENGTH: 36
<212> TYPE: DNA
<213> ORGANISM: Zea mays

<400> SEQUENCE: 18
ggggaatgct ggaatcgcaa tgcggtcctt gacagc                           36

<210> SEQ ID NO 19
<211> LENGTH: 20
<212> TYPE: DNA
<213> ORGANISM: Zea mays

<400> SEQUENCE: 19
taatttgttg aacagatccc                                             20

<210> SEQ ID NO 20
<211> LENGTH: 18
<212> TYPE: DNA
<213> ORGANISM: Zea mays

<400> SEQUENCE: 20
taaacaactt gtctaggg                                               18

<210> SEQ ID NO 21
<211> LENGTH: 18
<212> TYPE: DNA
<213> ORGANISM: Zea mays

<400> SEQUENCE: 21
cagatcccgg gatctgcg                                               18

<210> SEQ ID NO 22
<211> LENGTH: 20
<212> TYPE: DNA
<213> ORGANISM: Zea mays

<400> SEQUENCE: 22
gcgtctaggg ccctagacgc                                             20
```

CHIMERIC GENE COMPRISING INTRON FROM HISTONE H3.3 GENE

This application is a divisional of U.S. application Ser. No. 10/023,839, filed on Dec. 21, 2001, which is a continuation of U.S. application Ser. No. 09/000,062, filed on May 29, 1998, now U.S. Pat. No. 6,338,961, which was a national stage filing under 35 U.S.C. §371 of International Application No. PCT/FR96/01109, filed on Jul. 17, 1996.

The present invention relates to the use of a regulatory element isolated from transcribed plant genes, of new chimeric genes containing them and to their use for the transformation of plants.

Numerous phenotypic characters associated with the expression of one or more gene elements can be integrated into the genome of plants and thus confer on these transgenic plants advantageous agronomic properties. In a nonexhaustive manner, there may be mentioned: the resistances to pathogenic agents for crops, the resistance to phytotoxic plant-protection products, the production of substances of dietary or pharmacological interest. In addition to the isolation and characterization of the gene elements encoding these various characters, an appropriate expression should be ensured. This appropriate expression may be situated both at the qualitative and quantitative levels. At the qualitative level, for example the spatial level: preferential expression in a specific tissue, or temporal level: inducible expression; at the quantitative level, by the accumulated quantity of the product of expression of the gene introduced. This appropriate expression depends, for a large part, on the presence of regulatory gene elements associated with the transgenes, in particular as regards the quantitative and qualitative elements. Among the key elements ensuring this appropriate regulation, the use of single or combined homologous or heterologous promoter elements has been widely described in the scientific literature. The use of a regulatory element downstream of the transgene was used for the sole purpose of putting a boundary which makes it possible to stop the process of transcription of the transgene, without presupposition as to their role as regards the quality or the quantity of the expression of the transgene.

The present invention relates to the use of an intron 1 isolated from plant genes as a regulatory element, of new chimeric genes containing them and to their use for the transformation of plants. It relates to an isolated DNA sequence capable of serving as a regulatory element in a chimeric gene which can be used for the transformation of plants and allowing the expression of the product of translation of the chimeric gene in particular in the regions of the plant undergoing rapid growth, which comprises, in the direction of transcription of the chimeric gene, at least one intron such as the first intron (intron 1) of the noncoding 5' region of a plant histone gene. It relates more particularly to the simultaneous use of the intron 1 as a regulatory element and of promoters isolated from the same plant gene. It allows the appropriate expression, both quantitative and qualitative, of the transgenes under the control of these elements for gene regulation. This appropriate expression, obtained by the use of the present invention, may relate to characters such as: the resistance to pathogenic agents for crops, the resistance to phytotoxic plant-protection products, the production of substances of dietary or pharmacological interest. In particular, it makes it possible to confer on the transgenic plants an enhanced tolerance to herbicides by a qualitative and quantitative preferential expression of the product of expression of the chimeric genes in the regions of the plant undergoing rapid growth. This specific appropriate expression of the gene for herbicide resistance is obtained by the simultaneous use of the promoter regulatory elements and of at least one intron 1 of the histone gene of the "H3.3-like" type as regulatory element. Such a pattern of expression can be obtained for all the characters which are of interest, as described above, with the regulatory elements used to confer an enhanced herbicide tolerance. The present invention also relates to the plant cells transformed with the aid of these genes and the transformed plants regenerated from these cells as well as the plants derived from crossings using these transformed plants.

Among the plant-protection products used for the protection of crops, the systemic products are characterized in that they are transported in the plant after application and, for some of them, accumulate in the parts undergoing rapid growth, especially the caulinary and root apices, causing, in the case of herbicides, deterioration, up to the destruction, of the sensitive plants. For some of the herbicides exhibiting this type of behaviour, the primary mode of action is known and results from inactivation of characterized enzymes involved in the biosynthesis pathways of compounds required for proper development of the target plants. The target enzymes of these products may be located in various subcellular compartments and observation of the mode of action of known products most often shows a location in the plastid compartment.

Tolerance of plants sensitive to a product belonging to this group of herbicides, and whose primary target is known, may be obtained by stable introduction, into their genome, of a gene encoding the target enzyme, of any phylogenetic origin, mutated or otherwise with respect to the characteristics of inhibition, by the herbicide, of the product of expression of this gene. Another approach comprises introducing, in a stable manner, into the genome of sensitive plants a gene of any phylogenetic origin encoding an enzyme capable of metabolizing the herbicide into a compound which is inactive and nontoxic for the development of the plant. In the latter case, it is not necessary to have characterized the target of the herbicide.

Given the mode of distribution and accumulation of products of this type in the treated plants, it is advantageous to be able to express the product of translation of these genes so as to allow their preferential expression and their accumulation in the regions of the plant undergoing rapid growth where these products accumulate. Furthermore, and in the case where the target of these products is located in a cellular compartment other than the cytoplasm, it is advantageous to be able to express the product of translation of these genes in the form of a precursor containing a polypeptide sequence allowing directing of the protein conferring the tolerance into the appropriate compartment, and in particular in the plastid compartment.

By way of example illustrating this approach, there may be mentioned glyphosate, sulfosate or fosametine which are broad-spectrum systemic herbicides of the phosphonomethylglycine family. They act essentially as competitive inhibitors, in relation to PEP (phosphoenolpyruvate), of 5-enolpyruvylshikimate-3-phosphate synthase (EPSPS, EC 2.5.1.19). After their application to the plant, they are transported into the plant where they accumulate in the parts undergoing rapid growth, especially the caulinary and root apices, causing the deterioration, up to the destruction, of the sensitive plants.

EPSPS, the principal target of these products, is an enzyme of the pathway of biosynthesis of aromatic amino acids which is located in the plastid compartment. This enzyme is encoded by one or more nuclear genes and is synthesized in the form of a cytoplasmic precursor and then imported into the plastids where it accumulates in its mature form.

The tolerance of plants to glyphosate and to products of the family is obtained by the stable introduction, into their genome, of an EPSPS gene of plant or bacterial origin, mutated or otherwise with respect to the characteristics of inhibition, by glyphosate, of the product of this gene. Given the mode of action of glyphosate, it is advantageous to be able to express the product of translation of this gene so as to allow its high accumulation in the plastids and, furthermore, in the regions of the plant undergoing rapid growth where the products accumulate.

It is known, for example, from U.S. Pat. No. 4,535,060 to confer on a plant a tolerance to a herbicide of the above type, in particular N-phosphonomethylglycine or glyphosate, by introduction, into the genome of the plants, of a gene encoding an EPSPS carrying at least one mutation making this enzyme more resistant to its competitive inhibitor (glyphosate), after location of the enzyme in the plastid compartment. These techniques require, however, to be improved for greater reliability in the use of these plants during a treatment with these products under agronomic conditions.

In the present description, "plant" is understood to mean any differentiated multicellular organism capable of photosynthesis and "plant cell" any cell derived from a plant and capable of constituting undifferentiated tissues such as calli, or differentiated tissues such as embryos or plant portions or plants or seeds. "Intron 1 of *Arabidopsis* as a regulatory element" is understood to mean an isolated DNA sequence of variable length, situated upstream of the coding part or corresponding to the structural part of a transcribed gene. Gene for tolerance to a herbicide is understood to mean any gene, of any phylogenetic origin, encoding either the target enzyme for the herbicide, optionally having one or more mutations with respect to the characteristics of inhibition by the herbicide, or an enzyme capable of metabolizing the herbicide into a compound which is inactive and nontoxic for the plant. Zones of the plants undergoing rapid growth are understood to mean the regions which are the seat of substantial cell multiplications, in particular the apical regions.

The present invention relates to the production of transformed plants having an enhanced tolerance to herbicides accumulating in the zones of the treated plants undergoing rapid growth, by regeneration of cells transformed with the aid of new chimeric genes comprising a gene for tolerance to these products. The subject of the invention is also the production of transformed plants having an enhanced tolerance to herbicides of the phosphonomethylglycine family by regeneration of cells transformed with the aid of new chimeric genes comprising a gene for tolerance to these herbicides. The invention also relates to these new chimeric genes, as well as to transformed plants which are more tolerant because of a better tolerance in the parts of these plants undergoing rapid growth, as well as to the plants derived from crossings using these transformed plants. Its subject is also new intron 1 of a plant histone and its use as regulatory zone for the construction of the above chimeric genes.

More particularly, the subject of the invention is a chimeric gene for conferring on plants especially an enhanced tolerance to a herbicide having EPSPS as target, comprising, in the direction of transcription, a promoter element, a signal peptide sequence, a sequence encoding an enzyme for tolerance to the products of the phosphonomethylglycine family and a regulatory element, characterized in that the regulatory element comprises a fragment of an intron 1 of a plant histone gene in any orientation relative to its initial orientation in the gene from which it is derived, allowing the preferential expression and the accumulation of the protein for tolerance to the herbicide in the zones for accumulation of the said herbicide.

The histone gene, from which intron 1 according to the invention is derived, comes from a monocotyledonous plant such as for example wheat, maize or rice, or preferably from a dicotyledonous plant such as for example lucerne, sunflower, soya bean, rapeseed or preferably *Arabidopsis thaliana*. Preferably, a histone gene of the "H3.3-like" type is used.

The signal peptide sequence comprises, in the direction of transcription, at least one signal peptide sequence of a plant gene encoding a signal peptide directing transport of a polypeptide to a plastid, a portion of the sequence of the mature N-terminal part of a plant gene produced when the first signal peptide is cleaved by proteolytic enzymes, and then a second signal peptide of a plant gene encoding a signal peptide directing transport of the polypeptide to a sub-compartment of the plastid. The signal peptide sequence is preferably derived from a gene for the small subunit of ribulose-1,5-bisphosphate carboxylase/oxygenase (RuBisCO) according to European patent application PCT 508 909. The role of this characteristic sequence is to allow the release, into the plastid compartment, of a mature polypeptide with a maximum efficiency, preferably in a native form.

The coding sequence which can be used in the chimeric gene according to the invention comes from a herbicide tolerance gene of any phylogenetic origin. This sequence may be especially that of the mutated EPSPS having a degree of tolerance to glyphosate.

The promoter element according to European patent application PCT 507 698 may be of any origin, in a single or duplicated or combined form of a gene naturally expressed in plants, that is to say, for example of bacterial origin such as that of the nopaline synthase gene, or of viral origin such as that of the 35S transcript of the cauliflower mosaic virus, or preferably of plant origin such as that of the small subunit of the ribulose-1,5-bisphosphate carboxylase/oxygenase or preferably such as that of a plant histone gene and preferably from *Arabidopsis thaliana*. A histone gene of the "H4" type is preferably used.

The chimeric gene according to the invention may comprise, in addition to the above essential parts, an untranslated intermediate zone (linker) between the promoter zone and the coding zone as well as between the coding zone and intron 1 and which may be of any phylogenetic origin.

The following examples show by way of illustration, but with no limitation being implied, several aspects of the invention: isolation of the introns according to the invention and their use for the genetic transformation of plants as well as the improved qualities of expression of the heterologous genes of plants transformed with the aid of these introns. References to "Current Protocols in Molecular Biology" are to Volumes 1 and 2, Ausubel F. M. et al., published by Greene Publishing Associates and Wiley Interscience (1989) (CPMB).

EXAMPLE 1

1. Production of an EPSPS fragment from *Arabidopsis thaliana* a) two 20-mer oligonucleotides of respective sequences (SEQ ID NOS:8 and 9):

```
5'-GCTCTGCTCATGTCTGCTCC-3'

5'-GCCCGCCCTTGACAAAGAAA-3'
``` were synthesized from the sequence of an EPSPS gene from *Arabidopsis thaliana* (Klee H. J. et al., (1987) Mol. Gen.

Genet., 210, 437-442). These two oligonucleotides correspond to positions 1523 to 1543 and 1737 to 1717, respectively, of the published sequence and in convergent orientation.

b) The total DNA from *Arabidopsis thaliana* (var. *columbia*) was obtained from Clontech (catalogue reference: 6970-1)

c) 50 nanograms (ng) of DNA are mixed with 300 ng of each of the oligonucleotides and subjected to 35 amplification cycles with a Perkin-Elmer 9600 apparatus under the standard medium conditions for amplification recommended by the supplier. The resulting 204 bp fragment constitutes the EPSPS fragment from *Arabidopsis thaliana*.

2. Construction of a library of a cDNA from a BMS maize cell line.

a) 5 g of filtered cells are ground in liquid nitrogen and the total nucleic acids extracted according to the method described by Shure et al. with the following modifications:
the pH of the lysis buffer is adjusted to pH=9.0;
after precipitation with isopropanol, the pellet is taken up in water and after dissolution, adjusted to 2.5M LiCl. After incubation for 12 h at 0° C., the pellet from the 15 min centrifugation at 30,000 g at 4° C. is resolubilized. The LiCl precipitation stage is then repeated. The resolubilized pellet constitutes the RNA fraction of the total nucleic acids.

b) the RNA-poly A+ fraction of the RNA fraction is obtained by chromatography on an oligo-dT cellulose column as described in "Current Protocols in Molecular Biology".

c) Synthesis of double-stranded cDNA with an EcoRI synthetic end: it is carried out by following the procedure of the supplier of the various reagents necessary for this synthesis in the form of a kit: the "copy kit" from the company Invitrogen.

Two single-stranded and partially complementary oligonucleotides of respective sequences (SEQ ID NO:10):

```
5'-AATTCCCGGG-3'

5'-CCCGGG-3'
(the latter being phosphorylated)
``` are ligated to double-stranded cDNAs with blunt ends.

This ligation of the adaptors results in the creation of SmaI sites attached to the double-stranded cDNAs and of EcoRI sites in cohesive form at each end of the double-stranded cDNAs.

d) Creation of the library:

The cDNAs having at their ends the cohesive artificial EcoRI sites are ligated to the λgt10 bacteriophage cDNA cut with EcoRI and dephosphorylated according to the procedure of the supplier New England Biolabs.

An aliquot from the ligation reaction was encapsidated in vitro with encapsidation extracts: Gigapack Gold according to the supplier's instructions, this library was titrated using the bacterium *E. coli* C600hfl. The library thus obtained is amplified and stored according to the instructions of the same supplier and constitutes the cDNA library from BMS maize cell suspension.

3. Screening of the cDNA library from BMS maize cell suspension with the EPSPS probe from *Arabidopsis thaliana*:

The procedure followed is that of "Current Protocols in Molecular Biology". Briefly, about $10^6$ recombinant phages are plated on an LB plate at a mean density of 100 phages/$cm^2$. The lysis plaques are replicated in duplicate on a Hybond N membrane from Amersham.

The DNA was fixed onto the filters by a 1600 kJ UV treatment (Stratalinker from Stratagene). The filters were prehybridized in: 6×SSC/0.1% SDS/0.25 [lacuna] skimmed milk for 2 h at 65° C. The EPSPS probe from *Arabidopsis thaliana* was labelled with $^{32}$P-dCTP by random priming according to the instructions of the supplier (Kit Ready to Go from Pharmacia). The specific activity obtained is of the order of $10^8$ cpm per µg of fragment. After denaturation for 5 min at 100° C., the probe is added to the prehybridization medium and the hybridization is continued for 14 hours at 55° C. The filters are fluorographed for 48 h at –80° C. with a Kodak XAR5 film and intensifying screens Hyperscreen RPN from Amersham. The alignment of the positive spots on the filter with the plates from which they are derived make it possible to collect, from the plate, the zones corresponding to the phages exhibiting a positive hybridization response with the EPSPS probe from *Arabidopsis thaliana*. This step of plating, transfer, hybridization and recovery is repeated until all the spots of the plate of phages successively purified prove 100% positive in hybridization. A lysis plaque per independent phage is then collected in the diluent λ medium (Tris-Cl pH=7.5; 10 mM MgSO4; 0.1M NaCl; 0.1% gelatine), these phages in solution constituting the positive EPSPS clones from the BMS maize cell suspension.

4. Preparation and analysis of the DNA of the EPSPS clones from the BMS maize cell suspension About $5\times10^8$ phages are added to 20 ml of C600hfl bacteria at OD 2 (600 nm/ml) and incubated for 15 minutes at 37° C. This suspension is then diluted in 200 ml of growth medium for the bacteria in a 1 l Erlenmeyer flask and shaken in a rotary shaker at 250 rpm. Lysis is observed by clarification of the medium, corresponding to lysis of the turbid bacteria and occurs after about 4 h of shaking. This supernatant is then treated as described in "Current Protocols in Molecular Biology". The DNA obtained corresponds to the EPSPS clones from the BMS maize cell suspension.

One to two µg of this DNA are cut with EcoRI and separated on a 0.8% LGTA/TBE agarose gel (ref. CPMB). A final verification consists in ensuring that the purified DNA indeed exhibits a hybridization signal with the EPSPS probe from *Arabidopsis thaliana*. After electrophoresis, the DNA fragments are transferred onto Hybond N membrane from Amersham according to the Southern procedure described in "Current Protocols in Molecular Biology". The filter is hybridized with the EPSPS probe from *Arabidopsis thaliana* according to the conditions described in paragraph 3 above. The clone exhibiting a hybridization signal with the EPSPS probe from *Arabidopsis thaliana* and containing the longest EcoRI fragment has a gel-estimated size of about 1.7 kbp.

5. Production of the pRPA-ML-711 clone

Ten µg of DNA from the phage clone containing the 1.7 kbp insert are digested with EcoRI and separated on a 0.8% LGTA/TBE agarose gel (ref. CPMB). The gel fragment containing the 1.7 kbp insert is excised from the gel by BET staining and the fragment is treated with β-agarase according to the procedure of the supplier New England Biolabs. The DNA purified from the 1.7 kbp fragment is ligated at 12° C. for 14 h with DNA from the plasmid pUC 19 (New England Biolabs) cut with EcoRI according to the ligation procedure described in "Current Protocols in Molecular Biology". Two µl of the above ligation mixture are used for the transformation of one aliquot of electrocompetent *E. coli* DH10B; the transformation occurs by electroporation using the following conditions: the mixture of competent bacteria and ligation medium is introduced into an electroporation cuvette 0.2 cm thick (Biorad) previously cooled to 0° C. The physical electroporation conditions using an electroporator of Biorad trade mark are 2500 volts, 25 µFarad and 200Ω. Under these conditions, the mean condenser discharge time is of the order of 4.2 milliseconds. The bacteria are then taken up in 1 ml of SOC medium (ref. CPMB) and shaken for 1 hour at 200 rpm on a rotary shaker in 15 ml Corning tubes. After plating on LB/agar medium supplemented with 100 µg/ml of carbenicillin, the mini-preparations of the bacteria clones having grown overnight at 37° C. are carried out according to the procedure described in "Current Protocols in Molecular Biology". After digestion of the DNA with EcoRI and separation by electrophoresis on a 0.8% LGTA/TBE agarose gel (ref. CPMB), the clones having a 1.7 kbp insert are conserved. A final verification consists in ensuring that the purified DNA indeed exhibits a hybridization signal with the EPSPS probe from *Arabidopsis thaliana*. After electrophoresis, the DNA fragments are transferred onto a Hybond N membrane from Amersham according to the Southern procedure described in "Current Protocols in Molecular Biology". The filter is hybridized with the EPSPS probe from *Arabidopsis thaliana* according to the conditions described in paragraph 3 above. The plasmid clone having a 1.7 kbp insert and hybridizing with the EPSPS probe from *Arabidopsis thaliana* was prepared on a larger scale and the DNA resulting from the lysis of the bacteria purified on a CsCl gradient as described in "Current Protocols in Molecular Biology". The purified DNA was partially sequenced with a Pharmacia kit, following the supplier's instructions and using, as primers, the direct and reverse M13 universal primers ordered from the same supplier. The partial sequence produced covers about 0.5 kbp. The derived amino acid sequence in the region of the mature protein (about 50 amino acid residues) exhibits 100% identity with the corresponding amino sequence of the mature maize EPSPS described in U.S. Pat. No. 4,971,908. This clone, corresponding to a 1.7 kbp EcoRI fragment of the DNA for the EPSP from the BMS maize cell suspension, was called pRPA-ML-711. The complete sequence of this clone was obtained on both strands by using the Pharmacia kit procedure and by synthesizing oligonucleotides which are complementary and of opposite direction every 250 bp approximately.

The complete sequence of this 1713 bp clone obtained is presented by SEQ ID No. 1.

6. Production of the clone pRPA-ML-715

Analysis of the sequence of the clone pRPA-ML-711 and in particular comparison of the derived amino acid sequence with that from maize shows a sequence extension of 92 bp upstream of the GCG codon encoding the NH$_2$-terminal alanine of the mature part of the maize EPSPS (U.S. Pat. No. 4,971,908). Likewise, a 288 bp extension downstream of the AAT codon encoding the COOH-terminal asparagine of the mature part of the maize EPSPS (U.S. Pat. No. 4,971,908) is observed. These two parts might correspond, for the NH$_2$-terminal extension, to a portion of the sequence of a signal peptide before plastid location and, for the COOH-terminal extension, to the untranslated 3' region of the cDNA.

In order to obtain a cDNA encoding the mature part of the cDNA for the maize EPSPS, as described in U.S. Pat. No. 4,971,908, the following operations were carried out:

a) Elimination of the untranslated 3' region: construction of pRPA-ML-712:

The clone pRPA-ML-711 was cut with the restriction enzyme AseI and the resulting ends of this cut made blunt by treating with the Klenow fragment of DNA polymerase I according to the procedure described in CPMB. A cut with the restriction enzyme SacII was then performed. The DNA resulting from these operations was separated by electrophoresis on a 1% LGTA/TBE agarose gel (ref. CPMB).

The gel fragment containing the insert "AseI-blunt ends/SacII" of 0.4 kbp was excised from the gel and purified according to the procedure described in paragraph 5 above. The DNA of the clone pRPA-ML-711 was cut with the restriction enzyme HindIII situated in the polylinker of the cloning vector pUC19 and the ends resulting from this cut were made blunt by treating with the Klenow fragment of DNA polymerase I. A cut with the restriction enzyme SacII was then performed. The DNA resulting from these manipulations was separated by electrophoresis on a 0.7% LGTA/TBE agarose gel (ref. CPMB).

The gel fragment containing the insert HindIII-blunt ends/SacII of about 3.7 kbp was excised from the gel and purified according to the procedure described in paragraph 5 above.

The two inserts were ligated, and 2 µl of the ligation mixture served to transform *E. coli* DH1OB as described above in paragraph 5.

The plasmid DNA content of the various clones was analysed according to the procedure described for pRPA-ML-711. One of the plasmid clones retained contains an EcoRI-HindIII insert of about 1.45 kbp. The sequence of the terminal ends of this clone shows that the 5' end of the insert corresponds exactly to the corresponding end of pRPA-ML-711 and that the 3' terminal end has the following sequence (SEQ ID NO:11):

"5'. . . AATTAAGCTCTAGAGTCGACCTGCAGGCATGCAAGCT
T-3'".

The sequence underlined corresponds to the codon for the COOH-terminal amino acid asparagine, the next codon corresponding to the stop codon for translation. The nucleotides downstream correspond to sequence components of the polylinker of pUC19. This clone, comprising the sequence of pRPAML-711 up to the site for termination of translation of the mature maize EPSPS and followed by sequences of the polylinker of pUC19 up to the HindIII site, was called pRPA-ML-712.

b) Modification of the 5' End of pRPA-ML-712: Construction of pRPA-ML-715

The clone pRPA-ML-712 was cut with the restriction enzymes PstI and HindIII. The DNA resulting from these manipulations was separated by electrophoresis on a 0.8% LGTA/TBE agarose gel (ref. CPMB). The gel fragment containing the PstI/EcoRI insert of 1.3 kbp was excised from the gel and purified according to the procedure described in paragraph 5 above. This insert was ligated in the presence of an equimolar quantity of each of the two partially complementary oligonucleotides of sequence (SEQ ID NOS:12 AND 13):

Oligo 1:
5'-GAGCCGAGCTCCATGGCCGGCGCCGAGGAGATCGTGCTGCA-3'

Oligo 2:
5'-GCACGATCTCCTCGGCGCCGGCCATGGAGCTCGGCTC-3' as well as in the presence of DNA from the plasmid pUC19 digested with the restriction enzymes BamHI and HindIII.

Two µl of the ligation mixture served to transform *E. coli* DH1OB as described above in paragraph 5. After analysis of the plasmid DNA content of various clones according to the procedure described above in paragraph 5, one of the clones having an insert of about 1.3 kbp was conserved for subsequent analyses. The sequence of the terminal 5' end of the clone retained shows that the DNA sequence in this region is the following: sequence of the polylinker of pUC19 of the EcoRI to BamHI sites, followed by the sequence of the oligonucleotides used during the cloning, followed by the rest of the sequence present in pRPAML-712. This clone was called pRPA-ML-713. This clone has a methionine codon ATG included in an NcoI site upstream of the N-terminal alanine codon of the mature EPSPSynthase. Furthermore, the alanine and glycine codons of the N-terminal end were conserved, but modified on the third variable base: initial GCGGGT gives modified GCCGGC.

The clone pRPA-ML-713 was cut with the restriction enzyme HindIII and the ends of this cut made blunt by treating with the Klenow fragment of DNA polymerase I. A cut with the restriction enzyme SacI was then performed. The DNA resulting from these manipulations was separated by electrophoresis on a 0.8% LGTA/TBE agarose gel (ref. CPMB). The gel fragment containing the insert "HindIII-blunt ends/SacI" of 1.3 kbp was excised from the gel and purified according to the procedure described in paragraph 5 above. This insert was ligated in the presence of DNA from the plasmid pUC19 digested with the restriction enzyme XbaI and the ends of this cut made blunt by treating with the Klenow fragment of DNA polymerase I. A cut with the restriction enzyme SacI was then performed. Two µl of the ligation mixture served to transform *E. coli* DH10B as described above in paragraph 5. After analysis of the plasmid DNA content of various clones according to the procedure described above in paragraph 5, one of the clones having an insert of about 1.3 kbp was conserved for subsequent analyses. The sequence of the terminal ends of the clone retained shows that the DNA sequence is the following: sequence of the polylinker of pUC19 of the EcoRI to SacI sites, followed by the sequence of the oligonucleotides used during the cloning, from which the 4 bp GATCC of oligonucleotide 1 described above have been deleted, followed by the rest of the sequence present in pRPA-ML-712 up to the HindIII site and sequence of the polylinker of pUC19 from XbaI to HindIII. This clone was called pRPA-ML-715.

7) Production of a cDNA encoding a mature maize EPSPS

All the mutagenesis steps were carried out with the U.S.E. mutagenesis kit from Pharmacia, following the instructions of the supplier. The principle of this mutagenesis system is as follows: the plasmid DNA is heat-denatured and recombined in the presence of a molar excess, on the one hand, of the mutagenesis oligonucleotide and, on the other hand, of an oligonucleotide which makes it possible to eliminate a unique restriction enzyme site present in the polylinker. After the reassociation step, the synthesis of the complementary strand is performed by the action of T4 DNA polymerase in the presence of T4 DNA ligase and protein of gene 32 in an appropriate buffer provided. The synthesis product is incubated in the presence of the restriction enzyme, whose site is supposed to have disappeared by mutagenesis. The *E. coli* strain exhibiting, in particular, the mutS mutation is used as host for the transformation of this DNA. After growth in liquid medium, the total plasmid DNA is prepared and incubated in the presence of the restriction enzyme used above. After these treatments, the *E. coli* DH10B strain is used as host for the transformation. The plasmid DNA of the isolated clones is prepared and the presence of the mutation introduced is checked by sequencing.

A)—Site or sequence modifications with no effect a priori on the resistance character of maize EPSPS to the products which are competitive inhibitors of the activity of EPSP synthase: elimination of an internal NcoI site from pRPA-ML-715.

The sequence of pRPA-ML-715 is arbitrarily numbered by placing the first base of the N-terminal alanine codon GCC in position 1. This sequence has an NcoI site in position 1217. The site-modifying oligonucleotide has the sequence (SEQ ID NO:14):

5'-CCACAGGATGGCGATGGCCTTCTCC-3'.

After sequencing according to the references given above, the sequence read after mutagenesis corresponds to that of the oligonucleotide used. The NcoI site was indeed eliminated and translation into amino acids in this region conserves the initial sequence present in pRPA-ML-715.

This clone was called pRPA-ML-716.

The 1340 bp sequence of this clone is represented as SEQ ID No. 2 and SEQ ID No. 3.

B) Sequence modifications allowing an increase in the resistance character of maize EPSPS to products which are competitive inhibitors of the activity of EPSP synthase.

The following oligonucleotides (SEQ ID NOS:15, 16, 17 and 18) were used:

a) Thr 102→Ile mutation.

5'-GAATGCTGGAATCGCAATGCGGCCATTGACAGC-3' b) Pro 106→Ser mutation.

5'-GAATGCTGGAACTGCAATGCGGTCCTTGACAGC-3' c) Gly 101→Ala and Thr 102→Ile mutations.

5'-CTTGGGGAATGCTGCCATCGCAATGCGGCCATTG-3' d) Thr 102→Ile and Pro 106→Ser mutations.

5'-GGGGAATGCTGGAATCGCAATGCGGTCCTTGACAGC-3'

After sequencing, the sequence read after mutagenesis on the three mutated fragments is identical to the sequence of the parental DNA pRPA-ML-716 with the exception of the mutagenesis region which corresponds to that of the mutagenesis oligonucleotides used. These clones were called: pRPA-ML-717 for the Thr 102→Ile mutation, pRPA-ML-718 for the Pro 106→Ser mutation, pRPA-ML-719 for the Gly 101→Ala and Thr 102→Ile mutations and pRPA-ML-720 for the Thr 102→Ile and Pro 106→Ser mutations.

The 1340 bp sequence of pRPA-ML-720 is represented as SEQ ID No. 4 and SEQ ID No. 5.

The NcoI-HindIII insert of 1395 bp will be called in the rest of the descriptions "the double mutant of maize EPSPS".

EXAMPLE 2

Construction of Chimeric Genes

The construction of chimeric genes according to the invention is carried out using the following elements:

1). The genomic clone (cosmid clone c22) from *Arabidopsis thaliana*, containing two genes of the "H3.3-like" type was isolated as described in Chaubet et al. (J. Mol. Biol. 1992. 225 569-574).

2). Intron No. 1:

A DNA fragment of 418 base pairs is purified from digestion of the cosmid clone c22 with the restriction enzyme DdeI followed by treatment with a Klenow fragment of DNA polymerase from *E. coli*, according to the manufacturer's instructions for creating a blunt-ended DNA fragment and then cut with MseI. The purified DNA fragment is ligated to a synthetic oligonucleotide adaptor having the following sequence (SEQ ID NOS:19 and 20):

```
Adaptor 1:      5' TAATTTGTTGAACAGATCCC 3'
                   TAAACAACTTGTCTAGGG
```

The ligation product is cloned into pGEM7Zf(+) (Stratagene catalogue No. P2251) which was digested with SmaI. This clone, called "intron No. 1", is checked by sequencing (SEQ ID No. 6).

3). Intron No. 2:

A DNA fragment of 494 base pairs is purified from the digestion of the cosmid clone c22 with the restriction enzymes AluI and CfoI. The purified DNA fragment is ligated to a synthetic oligonucleotide adaptor having the following sequence (SEQ ID NOS:21 and 22):

```
Adaptor 2:      5' CAGATCCCGGGATCTGCG 3'
                   GCGTCTAGGGCCCTAGACGC
```

The ligation product is cloned into pGEM7Zf(+) (Stratagene catalogue No. P2251) which was digested with SmaI. This clone, called "intron No. 2", is checked by sequencing (SEQ ID No. 7).

4). pRA-1

The construction of this plasmid is described in French patent 9,308,029. This plasmid is a derivative of pBI 101.1 (Clonetech catalogue No. 6017-1) which contains the histone promoter from *Arabidopsis* H4A748 regulating the synthesis of the *E. coli* β-glucoronidase gene and of the nopaline synthase ("NOS") polyadenylation site. Thus, a chimeric gene is obtained having the structure:

"H4A748 promoter-GUS gene-NOS"

5). pCG-1

This plasmid contains the above intron No. 1 placed between the H4A748 promoter and the GUS coding region of pRA-1. This plasmid is obtained by digestion of cosmid clone c22 with BamHI and SmaI. The intron No. 1 of 418 base pairs is directly ligated into pRA-1 which was digested with BamHI and SmaI.

Thus, a chimeric gene is obtained having the structure:

"H4A748 promoter-intron No. 1-GUS gene-NOS"

6). pCG-13

This plasmid contains the above intron No. 2 placed between the H4A748 promoter and the GUS coding region of pRA-1. This plasmid is obtained by digestion of cosmid clone c22 with BamHI and SmaI. The intron No. 2 of 494 base pairs is directly ligated into pRA-1 which was digested with BamHI and SmaI.

Thus, a chimeric gene is obtained having the structure:

"H4A748 promoter-intron No. 2-GUS gene-NOS"

7). pCG-15

This plasmid contains only intron No. 1 before the above GUS coding sequence placed between the H4A748 promoter and the GUS coding region of pCG-1. This plasmid is obtained by digestion of pCG-1 with BamHI and HindIII followed by treatment with a Klenow fragment of DNA polymerase from *E. coli*, according to the manufacturer's instructions for creating a blunt-ended DNA fragment.

This vector is then religated to give a chimeric gene having the structure:

"intron No. 1-GUS-NOS"

8). pCG-18

This plasmid contains only the above intron No. 2 in front of the GUS coding sequence of pCG-13. This plasmid is obtained by partial digestion of pCG-13 with BamHI and SphI, followed by treatment with a fragment of T4 phage DNA polymerase, according to the manufacturer's instructions in order to create a blunt-ended DNA fragment.

This vector is then religated and checked by enzymatic digestion in order to give a chimeric gene having the structure:

"intron No. 2-GUS-NOS"

9). pRPA-RD-124

Addition of a "nos" polyadenylation signal to pRPA-ML-720 with creation of a cloning cassette containing the maize double mutant EPSPS gene (Thr 102→Ile and Pro 106→Ser). pRPA-ML-720 is digested with HindIII and treated with the Klenow fragment of DNA polymerase from *E. coli* in order to produce a blunt end.

A second digestion is carried out with NcoI and the EPSPS fragment is purified. The EPSPS gene is then ligated with purified pRPA-RD-12 (a cloning cassette containing the nopaline synthase polyadenylation signal) to give pRPA-RD-124. To obtain the purified useful vector pRPA-RD-12, it was necessary for the latter to be previously digested with SalI, treated with Klenow DNA polymerase, and then digested a second time with NcoI.

10). pRPA-RD-125

Addition of an optimized signal peptide (OSP) from pRPA-RD-124 with creation of a cloning cassette containing the EPSPS gene targeted on the plasmids. pRPA-RD-7 (European Patent Application EP 652 286) is digested with SphI, treated with T4 DNA polymerase and then digested with SpeI and the OSP fragment is purified. This OSP fragment is cloned into pRPA-RD-124 which was previously digested with NcoI, treated with Klenow DNA polymerase in order to remove the 3' protruding part, and then digested with SpeI. This clone is then sequenced in order to ensure the correct translational fusion between the OSP and the EPSPS gene. pRPA-RD-125 is then obtained.

11). pRPA-RD-196

In this plasmid, the "intron No. 1+β-glucoronidase gene from *E. coli*" portion of pCG-1 is replaced by a chimeric gene of 2 kilobases containing an optimized signal peptide, a double mutant EPSPS gene ($Ile_{102}$+$Ser_{106}$) and a nopaline synthase polyadenylation site ("NOS") isolated from pRPA-RD-125. To obtain pRPA-RD-196, the digestion of pCG-1 is performed with EcoRI and BamHI, followed by treatment with a Klenow fragment of DNA polymerase from *E. coli*, according to the manufacturer's instructions in order to create a blunt-ended DNA fragment. The 2-kilobase DNA fragment containing an optimized signal peptide of a double mutant EPSPS gene ($Ile_{102}$+$Ser_{106}$) and a nopaline synthase polyadenylation site ("NOS") is obtained from pRPA-RD-125 by digestion with NcoI and NotI, followed by treatment with DNA polymerase from *E. coli*, according to the manufacturer's instructions in order to create a blunt-ended DNA fragment. This blunt-ended fragment is then ligated into pCG-1 prepared above.

A chimeric gene is thus obtained having the structure:

"H4A748 promoter-OSP-maize EPSPS gene-NOS"

12). pRPA-RD-197

In this plasmid, the "β-glucoronidase gene from *E. coli*" portion of pCG-1 is replaced by a chimeric gene of 2 kilobases containing an optimized signal peptide, a double mutant EPSPS gene ($Ile_{102}$+$Ser_{106}$) and a nopaline synthase polyadenylation site ("NOS") isolated from pRPA-RD-125. To obtain pRPA-RD-197, the digestion of pCG-1 is performed with EcoRI, followed by treatment with a Klenow fragment of DNA polymerase from *E. coli*, according to the manufacturer's instructions in order to create a blunt-ended DNA fragment, then cut with SmaI. The 2-kilobase DNA fragment containing an optimized signal peptide, a double mutant EPSPS gene ($Ile_{102}$+$Ser_{106}$) and a nopaline synthase polyadenylation site ("NOS") is obtained from pRPA-RD-125 by digestion with NcoI and NotI, followed by a treatment with DNA polymerase from *E. coli*, according to the manufacturer's instructions in order to create a blunt-ended DNA fragment. This blunt-ended fragment is then ligated into pCG-1 prepared above.

A chimeric gene is thus obtained having the structure:
"H4A748 promoter-intron No. 1-maize EPSPS gene-NOS"

13). pRPA-RD-198

In this plasmid, the "β-glucoronidase gene from *E. coli*" portion of pCG-13 is replaced by a chimeric gene of 2 kilobases containing an optimized signal peptide, a double mutant EPSPS gene ($Ile_{102}$+$Ser_{106}$) and a nopaline synthase polyadenylation site ("NOS") isolated from pRPA-RD-125. To obtain pRPA-RD-198, the digestion of pCG-13 is performed with EcoRI, followed by treatment with a Klenow fragment of DNA polymerase from *E. coli*, according to the manufacturer's instructions in order to create a blunt-ended DNA fragment, then cut with SmaI. The 2-kilobase DNA fragment containing an optimized signal peptide, a double mutant EPSPS gene ($Ile_{102}$+$Ser_{106}$) and a nopaline synthase polyadenylation site ("NOS") is obtained from pRPA-RD-125 by digestion with NcoI and NotI, followed by a treatment with DNA polymerase from *E. coli*, according to the manufacturer's instructions in order to create a blunt-ended DNA fragment. This blunt-ended fragment is then ligated into pCG-13 prepared above.

A chimeric gene is thus obtained having the structure: "H4A748 promoter-intron No. 2-OSP-maize EPSPS gene-NOS"

EXAMPLE 3

Expression of the Activity of a Reporter Gene

1) Transformation and regeneration

The vector is introduced into the nononcogenic strain of *Agrobacterium tumefaciens* LBA 4404 available from a catalogue (Clontech #6027-1) by triparental crossing using the "helper" plasmid pRK 2013 in *Escherichia coli* HB101 according to the procedure described by Bevan M. (1984) Nucl. Acids Res., 12, 8711-8721.

The transformation technique using root explants of *Arabidopsis thaliana* L.-ecotype C24 was carried out according to the procedure described by Valvekens D. et al. (1988) Proc. Natl. Acad. Sci. USA, 85, 5536-5540. Briefly, 3 steps are necessary: induction of the formation of calli on Gamborg B5 medium supplemented with 2,4-D and kinetin; formation of buds on Gamborg B5 medium supplemented with 21P and IAA; rooting and formation of seeds on hormone-free MS.

2) Measurement of the GUS activity in plants a—Histochemical Observations

Visualization of the GUS activity by histochemical spots (Jefferson R. A. et al. (1987) EMBO J., 6, 3901-3907) on 10-day transgenic plants shows an increase in the intensity of the histochemical pattern which is tissue-specific for the plasmids containing the intron sequences (pCG-1 and pCG-13) compared with those without these introns (pRA-1). In particular, the pattern of spots for pCG-1 and pCG-13 is identical, showing an increase in intensity of the spots for the vascular and meristematic tissues, leaves and roots compared with that of the construct pRA-1. The constructs containing only the sequences of intron No. 1 (pCG-15 and pCG-18) show an extremely clear histochemical spot only in the apical meristem region.

b—Fluorometric Measurements

The GUS activity measured by fluorometry on extracts of floral and leaf buds of the rosette (Jefferson R. A. et al. (1987) EMBO J., 6, 3901-3907) from 12 plants, shows that the activity of the H4A748 promoter is increased under the influence of intron Nos. 1 and 2. Compared with the construct pRA-1, the GUS activity of pCG-1 and pCG-13 are at least six times greater in the floral buds, twenty times greater in the leaves of the rosette and twenty-six times greater in the roots.

These measurements clearly show that introns Nos. 1 and 2 of *Arabidopsis* histone genes of the "H3.3-like" type used as a regulatory element induces an increase in the activity of expression of the chimeric gene.

EXAMPLE 4

Tolerance of Transgenic Plants to a Herbicide

1) Transformation and regeneration

The vector is introduced into the nononcogenic strain of *Agrobacterium tumefaciens* LBA 4404 available from a catalogue (Clontech #6027-1) by triparental crossing using the "helper" plasmid pRK 2013 in *Escherichia coli* HB101 according to the procedure described by Bevan M. (1984) Nucl. Acids Res., 12, 8711-8721.

The transformation technique using foliar explants of tobacco is based on the procedure described by Horsh R. et al. (1985) Science, 227, 1229-1231. The regeneration of the PBD6 tobacco (origin SEITA-France) from foliar explants is carried out on a Murashige and Skoog (MS) basal medium comprising 30 g/l of sucrose as well as 200 µg/ml of kanamycin in three successive steps: the first comprises the induction of shoots on an MS medium supplemented with 30 g of sucrose containing 0.05 mg of naphthylacetic acid (NAA) and 2 mg/l of benzylaminopurine (BAP) for 15 days. The shoots formed during this step are then developed by culturing on an MS medium supplemented with 30 g/l of sucrose but not containing any hormone, for 10 days. The developed shoots are then removed and they are cultured on an MS rooting medium diluted one half, with half the content of salts, vitamins and sugars and not containing any hormone. After about 15 days, the rooted shoots are planted in the soil.

2) Measurement of the tolerance to glyphosate

Twenty transformed plants were regenerated and transferred to a greenhouse for each of the constructs pRPA-RD-196, pRPA-RD-197 and pRPA-RD-198. These plants were treated in a greenhouse at the 5-leaf stage with an aqueous suspension of herbicide, sold under the trademark RoundUp, corresponding to 0.8 kg of active substance glyphosate per hectare.

The results correspond to the observation of phytotoxicity values noted 3 weeks after treatment. Under these conditions, it is observed that the plants transformed with the constructs have on average an acceptable tolerance (pRPA-RD-196) or even a good tolerance (pRPA-RD-197 and pRPA-RD-198) whereas the untransformed control plants are completely destroyed.

These results show clearly the improvement offered by the use of a chimeric gene according to the invention for the same gene encoding tolerance to glyphosate.

The transformed plants according to the invention may be used as parents for producing lines and hybrids having the phenotypic character corresponding to the expression of the chimeric gene introduced.

The invention claimed is:

1. A method for preferentially expressing a chimeric gene in rapidly growing tissues of a transgenic plant, said method comprising transfecting plant cells with a chimeric gene comprising the first intron of the 5' non-translated region of a plant H3.3 histone gene as a regulatory element, and thereby causing the expression of said chimeric gene in rapidly growing tissues of said transgenic plant.

2. A method of making a chimeric gene comprising:
   obtaining a DNA molecule comprising a promoter sequence;
   obtaining a DNA molecule comprising an intron from the 5' non-coding region of a plant histone H3.3-like gene;
   obtaining a DNA molecule encoding a signal peptide sequence;
   obtaining a DNA molecule comprising a sequence encoding an enzyme;
   constructing the chimeric gene by linking the promoter sequence, the intron derived from the 5' non-coding region of a plant histone H3.3-like gene, the DNA encoding the signal peptide sequence and the sequence encoding an enzyme, optionally including one or more linker sequences.

3. The method of claim 2, wherein the sequence encoding an enzyme encodes a herbicide tolerance enzyme.

4. The method of claim 2, wherein the sequence encoding an enzyme encodes an EPSPS enzyme.

5. The method of claim 2, wherein obtaining a DNA molecule comprising an intron from the 5' non-coding region of a plant histone H3.3-like gene comprises isolating an intron from the 5' non-coding region of a gene in a plant genomic library that hybridizes under stringent conditions with a labeled histone H3.3 coding region probe.

6. The method of claim 5, wherein the plant is selected from among wheat maize or rice.

7. The method of claim 5, wherein the plant is selected from among lucerne, sunflower, soya bean, rapeseed, or Arabidopsis thaliana.

8. The method of claim 2, wherein the DNA molecule comprising an intron from the 5' non-coding region of a plant histone H3.3-like gene comprises a DNA sequence as described in SEQ ID NO: 6 or SEQ ID NO: 7.

9. A method of making a transgenic plant comprising obtaining a chimeric gene according to the method of claim 2, stably transforming plant cells with a DNA molecule comprising the chimeric gene, and growing a transgenic plant from said transformed plant cells.

10. A chimeric gene made by the method of claim 2.

11. A plant comprising as a transgene a chimeric gene made by the method of claim 2.

12. A chimeric gene comprising a promoter, an intron derived from the 5' non-translated region of a plant H3.3 histone gene, and a coding sequence.

* * * * *